United States Patent
Augagneur et al.

[11] Patent Number: 6,001,101
[45] Date of Patent: Dec. 14, 1999

[54] SCREW DEVICE WITH THREADED HEAD FOR PERMITTING THE COAPTATION OF TWO BONE FRAGMENTS

[75] Inventors: Christian Augagneur, Lyons; Louis Samuel Barouk, Yvrac, both of France

[73] Assignee: Depuy France, Villeurbanne, France

[21] Appl. No.: 08/782,455

[22] Filed: Jan. 13, 1997

Related U.S. Application Data

[63] Continuation of application No. 08/498,196, Jul. 5, 1995, abandoned.

[30] Foreign Application Priority Data

Jul. 5, 1994 [FR] France .................................... 94 08445

[51] Int. Cl.$^6$ .................................................. A61B 17/58
[52] U.S. Cl. ............................................ 606/73; 606/72
[58] Field of Search .............................. 606/72, 73, 60, 606/86

[56] References Cited

U.S. PATENT DOCUMENTS

| | | |
|---|---|---|
| 146,023 | 12/1873 | Russell . |
| 2,801,631 | 8/1957 | Charnley . |
| 4,175,555 | 11/1979 | Herbert . |
| 4,463,753 | 8/1984 | Gustilo ...................................... 606/73 |
| 5,019,079 | 5/1991 | Ross . |
| 5,300,076 | 4/1994 | Leriche ..................................... 606/73 |
| 5,370,662 | 12/1994 | Stone et al. ............................. 606/232 |
| 5,411,523 | 5/1995 | Goble ..................................... 606/232 |
| 5,569,248 | 10/1996 | Mathews .................................. 606/61 |

FOREIGN PATENT DOCUMENTS

| | | |
|---|---|---|
| 731381 | 4/1966 | Canada . |
| 0491211 | 11/1991 | European Pat. Off. . |
| 365613 | 4/1938 | Italy . |
| 8603666 | 7/1986 | WIPO . |
| 9109572 | 7/1991 | WIPO . |
| 9315682 | 8/1993 | WIPO . |

Primary Examiner—Michael Buiz
Assistant Examiner—Daphna Shai
Attorney, Agent, or Firm—Sughrue, Mion, Zinn, Macpeak & Seas, PLLC

[57] ABSTRACT

A screw device for the coaptation of two small bone fragments includes a threaded proximal head part and a threaded distal part, the proximal part having a diameter greater than the distal part and having a thread pitch smaller than that of the distal part. The distal part is threaded over substantially its entire length and a short length smooth portion is provided between the proximal and distal parts. The upper edges of the threads of the two threaded parts are perpendicular to the axis of the thread, while their lower edges are oblique, and each threaded part has at its base at least one tapping notch. An axial channel is provided in the screw for permitting the use of a guide pin.

7 Claims, 3 Drawing Sheets

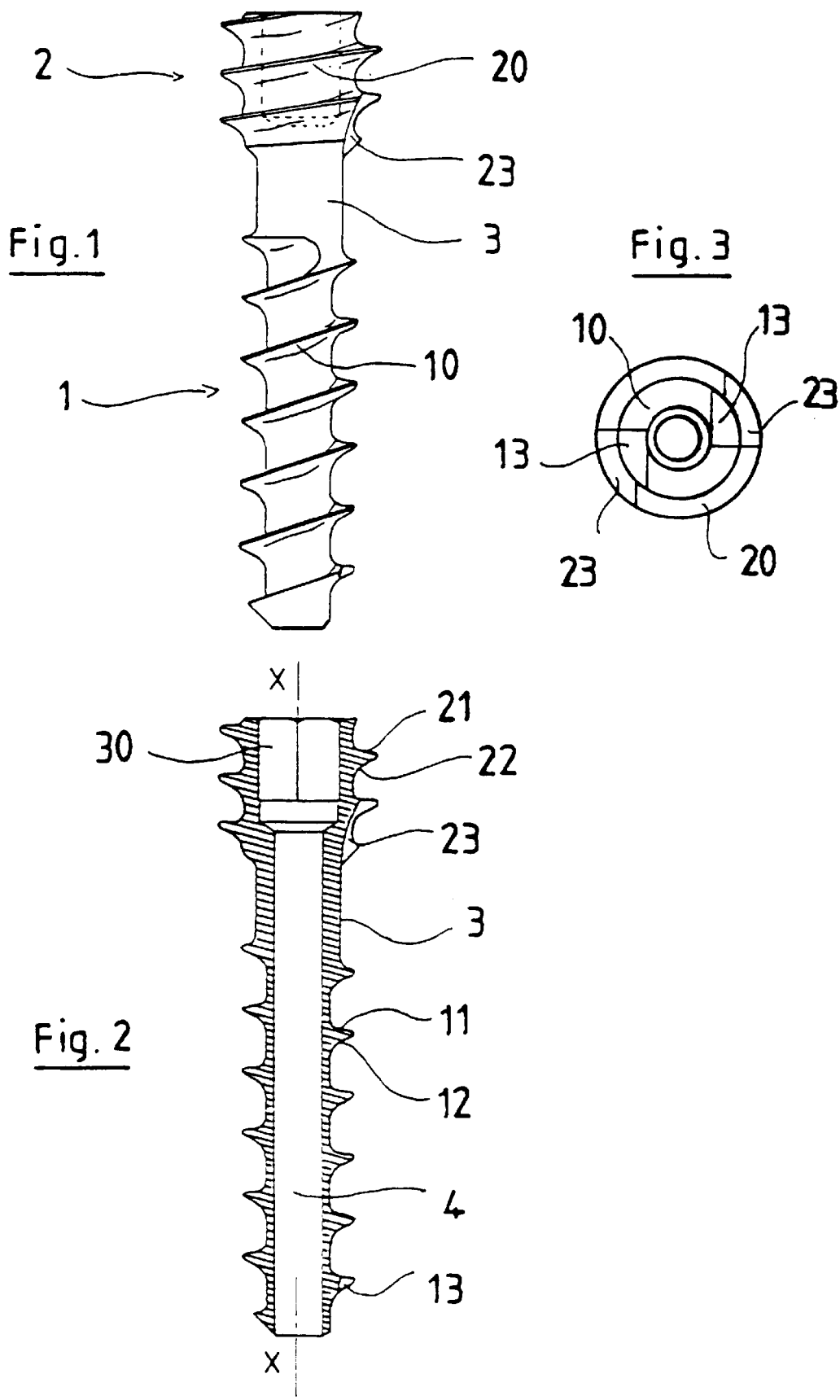

SCREW DEVICE WITH THREADED HEAD FOR PERMITTING THE COAPTATION OF TWO BONE FRAGMENTS

This application is a continuing application of U.S. Pat. No. 08/498,196, filed on Jul. 5, 1995, now abandoned.

The present invention relates to orthopedic surgery and specifically to a screw device intended to permit the coaptation of two bone fragments in foot surgery.

More particularly, the present invention is directed to the treatment of hallux valgus by the so called SCARF osteotomy: the hallux valgus is a deformation of the big toe, the metarsal bone of which is oriented to the outside of the foot, specifically for women using pointed shoes such ballet dancers.

According to the SCARF osteotomy method, the metatarsal bone is longitudinally and transversely cut; afterwards one of the bone fragments called "beam" is moved laterally to locate it closer to the other toes of the foot. The surgeon inserts screws in order to obtain a coaptation of the two bone fragments and finally cuts the laterally extending portion of the bone fragment which has not been moved.

In the known prior art, the U.S. Pat. No. 4,175,555 HERBERT teaches a screw having two proximal and distal threaded parts between which a long smooth part is arranged and has a diameter intermediate between the diameter of the crests and that of the root of the distal part. The proximal part has threads the diameter of which is substantially equal to the diameter of the crests of the distal part, and the thread of the proximal part has a smaller pitch than the pitch of the distal part.

The screwing of such screw into a previously drilled and tapped orifice in the two bone fragments to be joined has the effect, due to the difference in the pitches, of a faster penetration of the distal part, which results in a bringing together of the two bone fragments. This bringing together is accentuated by the configurations of the threads, which comprise an edge which is perpendicular to the axis of the screw, namely the lower edge in the case of the proximal part and the upper edge in the case of the distal part.

The screw disclosed in this HERBERT patent is suitable a well for small bones surgery, in particular foot surgery, as for long bones surgery such as femur and tibia. It's smooth portion is very long compared to the threaded portions, since this smooth part must be located at the level of the fracture line. Consequently the length of the threaded distal portion is short and the compression of the two bone portions to be assembled by the screw is limited to the cortical thickness of the bone. The obtained compression of the two bone fragments one on the other is therefore relatively weak, the spongy portion inside the bone being not used to this end.

Now, for surgery of hallux valgus, the screw must be very small since the bones are small, but additionally the screw must be able to anchor itself at the most, which is not possible with the long smooth portion of the prior HERBERT screw.

Additionally, this prior screw is not self-tapping, so that before screwing the bone periosteum must be removed, and damaged, to create an insertion orifice, which for small bones is a serious drawback that should be avoided.

SUMMARY OF THE INVENTION

The object of the present invention is a screw device of the above mentioned kind which makes it possible to overcome these drawbacks of the prior art.

The screw device according to the invention is adapted to permit the coaptation of two small bone fragments, comprises a threaded proximal head part and a threaded distal part, the proximal part having a diameter higher than the distal part and having a thread pitch smaller that than of said distal part; the distal part is threaded over substantially its entire length and a short length smooth portion is provided between said proximal and distal parts, the upper edges of the threads of the two threaded parts are perpendicular to the axis of the thread, while their lower edges are oblique, and each threaded part has at its base at least one tapping notch.

According to another feature of the invention, and axial channel is provided in the screw for permitting the use of a guide pin.

Other features and advantages of the present invention will more clearly appear from the following description in reference to the enclosed drawings, which show an embodiment of the invention. On the enclosed drawings:

BRIEF DESCRIPTION OF THE DRAWINGS

FIG. 1 is an elevation view of a screw device according to the invention,

FIG. 2 shows a screw in longitudinal section along a median plane of the device of FIG. 1.

FIG. 3 is a plan face view of the distal end of the screw device.

DESCRIPTION OF THE DRAWINGS

Referring to FIG. 1, it can be seen that a screw device in accordance with the invention comprises a long threaded distal part 1 and a short threaded proximal head part 2, having a diameter greater than that of the distal part 1.

Figure 4:
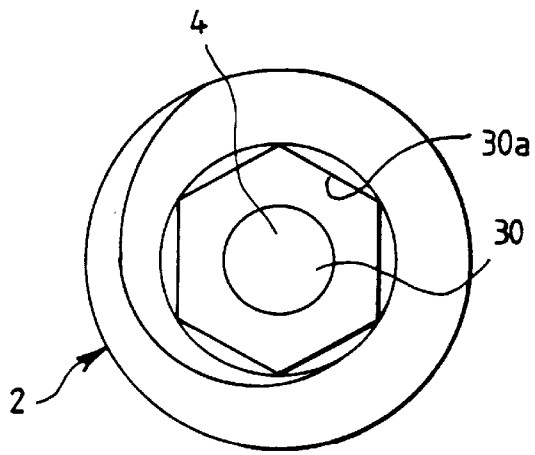
FIG. 4 is a plan face view of the proximal end of the device.

A hole 30 is formed within the proximal portion 2 and has a polygonal contour (hexagonal 30*a* as shown on FIG. 4) adapted to receive a corresponding screwing tool. This hole 30 is extended within the smooth portion 3 and distal portion 1 by an axial channel 4 permitting the insertion therein of a guiding pin (not shown) for screwing.

The threads are of different pitch, the pitch of the thread 10 of the distal part 1 being greater than the pitch of the thread 20 of the proximal part 2.

Figure 5:
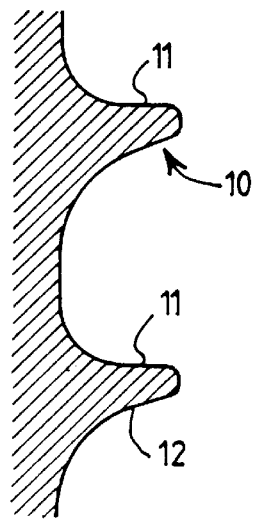
FIG. 5 is an enlarged partial cross-section view showing the threads of the distal portion of the screw of FIGS. 1–4.

Referring also to FIGS. 2 and 5 it can be seen that the upper edges 11 and 21 of the threads 10 and 20 respectively are perpendicular to the axis XX of the screw, while the lower sides, 12 and 22 respectively, are oblique in regard to this axis.

Each lower end of the distal part 1 and proximal part 2 comprises a lateral notch, 13 and 23 respectively. These notches are diametrically opposite each other and are intended to permit self-tapping, in combination with the configuration of the threads 10 and 20, namely the obliqueness of the lower sides 12 and 22.

Between the distal part 1 and the proximal part 2, the screw is provided with a smooth section 3, the length of which is very short in regard to the length of the threaded distal part 1. Possibly this smooth portion can even be removed or be limited to the manufacturing requirements, since technically it is difficult to manufacture two threads without any gap between them.

As a result of the lateral shifting of one bone fragment with respect to the other, the screw is normally embedded in the periphery of the bones. This means that the proximal part and at least the end of the distal part are anchored in the cortex, upper and lower respectively, and that the central part of the distal part is anchored costally in the lateral cortex.

In the treatment of hallux valgus, it also frequently happens, when treating the first metatarsal, that it is necessary, in addition to the anchoring in the upper and lower cortexes, to pass through the lateral cortex, which requires that the median part of the screw be threaded in order to assure the anchoring thereof.

The device of the invention can be made of any biocompatible metal material, for instance titanium or TA 6 V, or chrome-cobalt alloy, or of stainless steel. It can also be made of a biodegradable and/or biocompatible material, or of a biointegratable inorganic material, for instance calcium phosphate or hydroxyapatite.

As the screw is completely insertable, it does not have to be removed, so that it is advantageous to use a biointegratable material.

Figure 6:
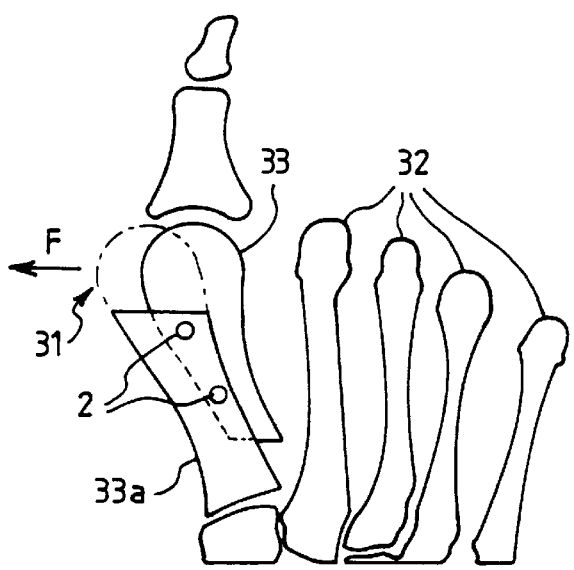
FIG. 6 is a schematic plan view of foot bones, the big toe having an hallux valgus to be treated.
Figure 7:
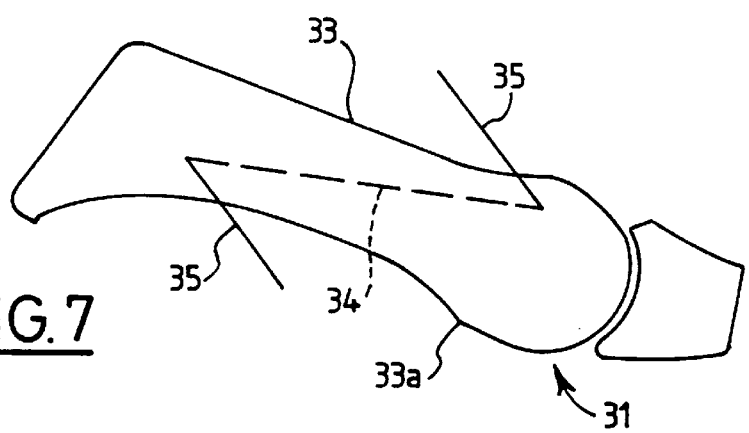
FIG. 7 is an enlarged longitudinal side view of the big toe of FIG. 6 showing the longitudinal and transverse cut line of the metatarsal bone to be treated.
Figure 8:
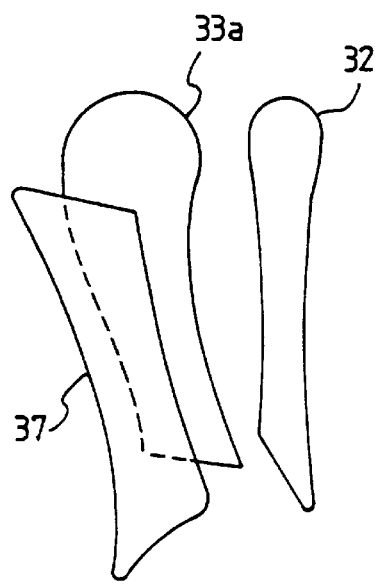
FIG. 8 is a plan view showing the final position of the beam of the metatarsal bone of FIG. 7.

FIGS. 6, 7, 8 schematically illustrate the hallux valgus treatment. Among the five foot fingers 31, 32, the big toe 31 is deformed in the outside direction (arrow F and shown in dots and dashes points). The surgical method of treatment of this hallux valgus consists, in abstract, to longitudinally cut the metatarsal bone 33 along a longitudinal line 34 and transverse lines 35 inclined on angles of 45° on the longitudinal cut line 34. In a further step, the surgeon laterally moves to the inside direction, i.e. towards fingers 32, the lower bone fragment 33a (called the "beam"). Afterwards the surgeon inserts fixation screws in order to firmly assembly and compress on each other the two bone fragments 33 and 33a (FIGS. 9–10).

Finally the surgeon partly cuts the side bone portion 37 forming a lateral extension with respect to the bone fragment 33a (FIG. 8).

Figure 9:
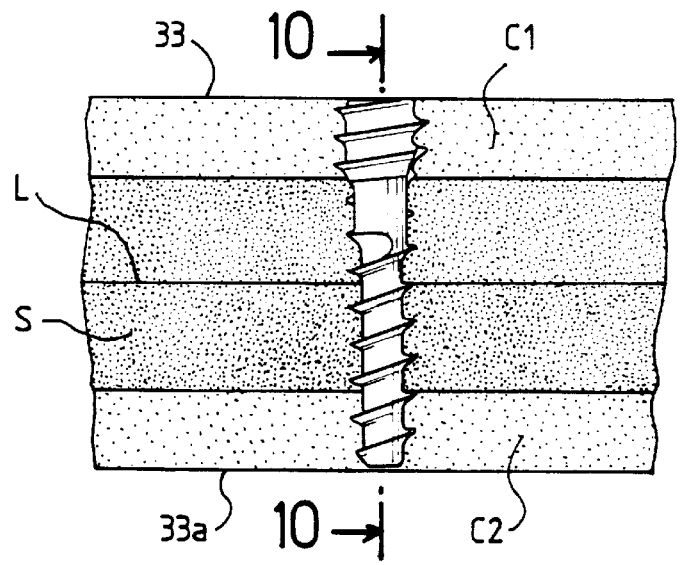
FIG. 9 shows a screw according to the invention inserted inside two bone fragments to be coapted.
Figure 10:
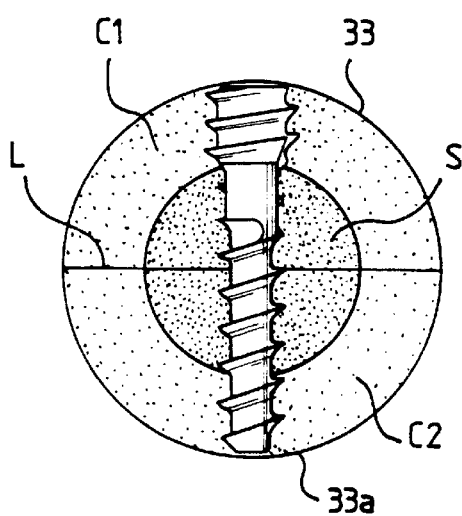
FIG. 10 is a cross-section view according to line 10—10 of FIG. 9.

On FIGS. 9 and 10, it can be easily understood that the long threaded portion 1 of the screw and the correspondingly very short smooth portion 3 (possibly cancelled) permit to obtain a high compression of the two bone fragments 33, 33a one on each other during screwing. Indeed, not only the cortical portion C1, C2 of the bone are used to that end, but also inside spongy portion S, on each side of the fracture line L.

This compression effect of the two bone fragments 33, 33a comes from the difference between pitches of the threaded portions 1 and 2: during a complete revolution of the screw about its longitudinal axis XX, the travel of the distal part 1 is higher than the travel of the proximal part 2; since the proximal part is integer with the distal part, it is driven by the latter, with fragment 33, so that this difference between pitches entails a compression of the two bone fragments 33, 33a one on each other.

Finally the screw according to the invention has a combination of very advantageous means:

it is self-compressive, due to the difference between pitches of the two threaded portions, it is self-tapping due to the tapping notches 13, 23, it does not generate any trauma due to the fact that its head 2 is entirely threaded and consequently completely embedded within the bone (FIGS. 9–10) after screwing.

It can be very accurately inserted within the bone, due to its axial channel 4 which permits the use of a guide pin.

What is claimed is:

1. A screw device having an axis and adapted to permit a coaptation of two small bone fragments, said screw device comprising an axially extending threaded proximal cylindrical head upper part (2) and an axially extending threaded cylindrical distal lower part (1), wherein said proximal part has a diameter greater than that of the distal part, and has a thread pitch smaller than that of said distal part, wherein the distal part is threaded over substantially its entire length, and a shorter length smooth portion (3) is provided between said proximal and distal parts, wherein upper edges (11, 21) of the threads of both threaded parts (1, 2), are perpendicular to said axis, while their lower edges (12, 22) are oblique to said axis, wherein at least one tapping notch (13, 23) is formed in each threaded part (1, 2) and wherein said device further comprises an axially extending hollow channel for receiving a guide pin.

2. A device according to claim 1, wherein diametrically opposite notches (13;23) are formed in respective end portions of said proximal part and said distal part.

3. A device according to claim 1, made of a biodegradable and biocompatible material.

4. The device according to claim 1, made of a biointegratable material.

5. A device according to claim 1, made of a biocompatible material.

6. The device according to claim 1, wherein the thread pitch of the proximal head part is 1 mm±0.02, the thread pitch of the distal part is 1.34 mm±0.02, and the angle between the upper and lower thread edges is 25 degrees.

7. The device according to claim 1, wherein said shorter length of said smooth portion is substantially zero, being only long enough to satisfy manufacturing requirements of the screw device.

* * * * *